(12) United States Patent
Scharf et al.

(10) Patent No.: US 8,700,119 B2
(45) Date of Patent: *Apr. 15, 2014

(54) METHOD AND DEVICE FOR DETERMINING AND PRESENTING SURFACE CHARGE AND DIPOLE DENSITIES ON CARDIAC WALLS

(71) Applicant: Christoph Scharf, Zurich (CH)

(72) Inventors: Christoph Scharf, Zurich (CH); Gunter Scharf, Zurich (CH)

(73) Assignee: Christoph Scharf, Horgen (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/858,715

(22) Filed: Apr. 8, 2013

(65) Prior Publication Data

US 2013/0226017 A1    Aug. 29, 2013

Related U.S. Application Data

(63) Continuation of application No. 12/376,270, filed as application No. PCT/CH2007/000380 on Aug. 3, 2007, now Pat. No. 8,417,313.

(30) Foreign Application Priority Data

Aug. 3, 2006   (CH) ....................................... 1251/06

(51) Int. Cl.
*A61B 5/042*   (2006.01)

(52) U.S. Cl.
USPC ............................ 600/374; 600/508; 600/509

(58) Field of Classification Search
USPC ............................................ 600/508, 374, 509
See application file for complete search history.

(56) References Cited

U.S. PATENT DOCUMENTS

| | | | |
|---|---|---|---|
| 5,795,298 A | 8/1998 | Vesely et al. |
| 6,066,096 A | 5/2000 | Smith et al. |
| 6,301,496 B1 | 10/2001 | Reisfeld |
| 6,400,981 B1 | 6/2002 | Govari |
| 6,640,119 B1 | 10/2003 | Budd et al. |
| 6,728,562 B1 | 4/2004 | Budd et al. |
| 6,826,420 B1 | 11/2004 | Beatty et al. |
| 6,826,421 B1 | 11/2004 | Beatty et al. |
| 6,990,370 B1 | 1/2006 | Beatty et al. |

(Continued)

FOREIGN PATENT DOCUMENTS

| | | |
|---|---|---|
| EP | 1166714 | 1/2002 |
| EP | 1760661 | 3/2007 |

(Continued)

OTHER PUBLICATIONS

International Search Report and Written Opinion dated Mar. 5, 2013, issued in related International Application No. PCT/US2012/028593.

(Continued)

*Primary Examiner* — Allen Porter, Jr.
(74) *Attorney, Agent, or Firm* — Onello & Mello, LLP

(57) ABSTRACT

The invention discloses a method, a system, a computer program and a device for determining the surface charge and/or dipole densities on heart walls. Using the foregoing, a table of dipole densities ν(P', t) and/or a table of surface charge densities ρ(P', t) of a given heart chamber can be generated.

22 Claims, 4 Drawing Sheets

(56) References Cited

U.S. PATENT DOCUMENTS

| | | | |
|---|---|---|---|
| 7,289,843 | B2 | 10/2007 | Beatty et al. |
| 7,505,810 | B2 | 3/2009 | Harlev et al. |
| 7,841,986 | B2 | 11/2010 | He et al. |
| 7,953,475 | B2 | 5/2011 | Harlev et al. |
| 8,417,313 | B2 | 4/2013 | Scharf et al. |
| 2003/0231789 | A1 | 12/2003 | Willis et al. |
| 2009/0264781 | A1 | 10/2009 | Scharf |
| 2010/0298690 | A1 | 11/2010 | Scharf |
| 2011/0270237 | A1 | 11/2011 | Werneth et al. |

FOREIGN PATENT DOCUMENTS

| | | |
|---|---|---|
| WO | 94/06349 | 3/1994 |
| WO | 00/07501 | 2/2000 |
| WO | 2008014629 | 2/2008 |
| WO | 2009090547 | 7/2009 |
| WO | 2011136867 | 11/2011 |

OTHER PUBLICATIONS

International Search Report dated Oct. 7, 2009 issued in related International Application No. PCT/IB2009/000071.

Della Bella P., et al., "Non-contact mapping to guide catheter ablation of untolerated ventricular tachycardia," European Heart Journal, May 2002, vol. 23, No. 9, pp. 742-752.

Pullan, Andrew, et al., "The Inverse Problem of Electrocardiography," Northeastern University Electrical and Computer Engineering, Feb. 23, 2007.

Christoph Scharf, et al., Declaration under 37 C.F.R. 1.132, Nov. 15, 2012.

He, et al., "An Equivalent Body Surface Charge Model Representing Three-Dimensional Bioelectrical Activity," IEEE Transactions on Biomedical Engineering, 42.7 (1995), pp. 637-646.

International Search Report issued in corresponding PCT application No. PCT/CH2007/000380.

"Method and Device for Determining and Presenting Surface Charge and Dipole Densities on Cardiac Walls" Specification, Drawings, Claims and Prosecution History of U.S. Appl. No. 12/376,270, filed Feb. 3, 2009 by Christoph Scharf, et al.

METHOD AND DEVICE FOR DETERMINING AND PRESENTING SURFACE CHARGE AND DIPOLE DENSITIES ON CARDIAC WALLS

CROSS REFERENCE TO RELATED APPLICATIONS

The present application is a continuation application of U.S. patent application Ser. No. 12/376,270, filed on Feb. 3, 2009, which is a 371 national stage application of Patent Cooperation Treaty Application No. PCT/CH2007/000380 filed Aug. 3, 2007, entitled METHOD AND DEVICE FOR DETERMINING AND PRESENTING SURFACE CHARGE AND DIPOLE DENSITIES ON CARDIAC WALLS, which is incorporated herein by reference, which in turn claims priority to Swiss Patent Application 1251/06 filed Aug. 3, 2006.

FIELD OF INVENTION

The invention relates to a method, a system, a computer program and a device for determining the surface charge and/or dipole densities on heart walls in order to locate the origin(s) of cardiac arrhythmias.

BACKGROUND

For localizing the origin(s) of cardiac arrhythmias it is common practice to measure the electric potentials located on the inner surface of the heart by electrophysiological means within the patient's heart. For example, for this purpose electrode catheters can be inserted into the heart and moved around while recording cardiac potentials during normal heart rhythm or cardiac arrhythmia. If the arrhythmia has a regular activation sequence, the timing of the electric activation measured in voltages at the site of the electrode can be integrated when moving the electrode around during the arrhythmia, to create a three dimensional map of the electric activation. By doing this, information on the localization of the source of arrhythmia(s) and mechanisms, i.e., reentry circuits, can be diagnosed to initiate or guide treatment (radiofrequency ablation).

This mapping procedure is often aided by computer systems generating three dimensional maps of catheter positions by localizing the catheter with the help of magnetic fields (the so called Carto System) or transthoracic impedances (by Localisa and NavX). Because all the points of such maps are obtained by electrode positions in contact with the cardiac surface, this mapping system is called contact mapping. It has the inherent limitation that cardiac activation can only be assessed simultaneously at the points in contact with the myocardium. Hence, an instant map of the entire cardiac activation is impossible because the entire heart chamber cannot be contacted without compromising blood circulation. An instant mapping of the simultaneous electric activation of the heart chamber, however, might be of advantage in unstable arrhythmias of short duration, rendering the mapping procedures (moving the electrode around during the arrhythmia) too long. In addition, an instant map of cardiac electric activation might be of advantage during irregular arrhythmias or arrhythmias with non-constant activation sequences that render integration of activation times from contact mapping impossible. Finally, instant maps of cardiac activation are probably also faster and easier obtained, than a contact map generated by time consuming catheters movements to different areas of the heart in all sorts of cardiac arrhythmias.

The disadvantage of contact mapping can be overcome by "non-contact mapping", which allows for mapping cardiac activation of a heart chamber simultaneously without contact to the cardiac wall. For this purpose, for instance, a multi electrode array mounted on an inflatable balloon can be inserted into the heart. The geometry of the heart chamber is obtained either (i) by reconstruction of a contact map, which is obtained from integration of movements with an electrode catheter within the heart chamber, or (ii) by importing imaging data from computed tomography or MRI (magnetic resonance imaging).

Once the geometry of the cardiac chamber is outlined in a map the information of a simultaneous recording of cardiac farfield potentials (unipoles) by the multi electrode array can be extrapolated to the desired cardiac map using advanced mathematical methods. This non-contact mapping has the advantage that it provides the entire electric activation measured by farfield unipolar potentials either in sinus rhythm or during arrhythmia without the need for moving an electrode catheter around the cardiac chamber. This allows for a beat to beat analysis of cardiac activation and, therefore, unstable, irregular or multifocal arrhythmias can be tracked and treated. However, the disadvantage of non-contact mapping is that it relies on farfield potentials, which do not allow for the same precision in localization as contact mapping (i.e. measuring local electrograms (potentials) of cardiac activation by touching the endocardium at the site of interest with a mapping electrode).

Furthermore, non-contact mapping is more prone to artifact generation and interference from potentials generated by cardiac re-polarization and adjacent heart chambers (atria/ventricles). These drawbacks can be overcome to a certain extent with several filtering techniques. One the other side, in many cases these drawbacks also render the localization of cardiac arrhythmias a time-consuming frustrating intervention.

Therefore, the advantages of non-contact mapping, i.e. the instant cardiac activation maps, have to be balanced against the disadvantages, i.e. the decreased spatial resolution due to recording of far field signals, filtering of artifacts, etc.

Finally, another method for the non-invasive localization of cardiac arrhythmics is body surface mapping. In this technique multiple electrodes are attached to the entire surface of the thorax and the information of the cardiac electrograms (surface ECG) is measured in voltages integrated to maps of cardiac activation. Complex mathematical methods are required in order to determine the electric activation in a heart model, for instance, one obtained from CT or MRI imaging giving information on cardiac size and orientation within the thoracic cavity.

The disadvantage of both mapping methods, i.e. contact and non-contact types, is the representation of the electric activity of the heart by means of potentials, that are the result of a summation of electric activities of many cardiac cells. The integration of all these local electric ion charges generated by the cardiac cells provides for the potentials that are measured by current mapping systems.

Therefore, it is an object of the present invention to provide a method, a system, a program and a device for improving precision, accuracy and spatial resolution of cardiac activation mapping, when compared to prior art systems.

SUMMARY OF INVENTION

It was surprisingly found that the use of surface charge and/or dipole densities and in particular their distribution in a heart chamber is a much better indicator of cardiac arrhythmias than electric potentials in the heart.

In a first aspect, the present invention relates to a method for determining a database table of surface charge densities ($\rho$) of at least one given heart chamber, the surface charge density information comprising a table (data values) $\rho(P', t)$, wherein:

i) the position $P'=(x',y',z')$ of a point at the wall of the heart is defined in x, y, z-coordinates, ii) t is the time of measurement for said surface charge density, and iii) $\rho$ is the surface charge density at said time t and said position P' derived from a measured electric potential from a given heart chamber, comprising the following steps:

a) measuring and/or calculating one or more electric potential(s) $V_e$ in one or more position(s) P at a given time t, and b) transforming $V_e$ into said charge density $\rho(P',t)$ by using an algorithm suitable for transforming an electric potential into surface charge density.

In another aspect, the present invention relates to a method for determining a database table of dipole densities $v(P',t)$ of at least one given heart chamber, the dipole density information comprising a table (data values) $v(P', t)$, wherein:

i) the position $P'=(x',y',z')$ of a point at the wall of the heart is defined in x, y, z-coordinates, ii) t is the time of measurement for said dipole density, and iii) v is the dipole density at said time t and said position P' derived from a measured electric potential $V_e$ from a given heart chamber, comprising the following steps:

a) measuring and/or calculating one or more electric potential(s) $V_e$ in one or more positions P at a given time t, and b) transforming $V_e$ into said dipole density $v(P',t)$ by using an algorithm suitable for transforming an electric potential into surface charge density.

Preferably, the electric potential(s) $V_e$ can be determined by contact mapping. Equally preferred the electric potential(s) $V_e$ can be determined by non-contact mapping.

In one embodiment, the above mentioned algorithm method for transforming said $V_e$ into surface charge density ($\rho$) or dipole density (v) in step b) above employs the boundary element method (BEM).

The geometry of the probe electrode can be ellipsoidal or spherical.

In one embodiment, the measured potential(s) $V_e$ can be transformed into surface charge densities $\rho$ using the following equation:

$$V_e(P) = -\frac{1}{4\pi} \int_{S_e} \frac{\rho(P')}{|P'-P|} d\sigma(P') \quad (4)$$

wherein:

Se=surface of endocardium;

P'=integration variable running over the entire cardiac wall; and

P=Position of the measuring electrode.

In another embodiment, the measured potential(s) $V_e$ can be transformed into dipole densities v using the following equation:

$$V_e(P) = \frac{1}{4\pi} \int_{S_e} v(P') \frac{\partial}{\partial n_{P'}} \frac{1}{|P-P'|} d\sigma(P') \quad (5)$$

wherein:

Se=surface of endocardium;

P'=integration variable running over the entire cardiac wall; and

P=Position of the measuring electrode.

According to a further aspect of the present invention, provided is a system for determining a table of surface charge densities $\rho(P', t)$ of a given heart chamber, comprising:

a) one unit for measuring and recording at least one electric potential $V_e$ at a given position P, b) one a/d-converter for converting the measured electric potentials into digital data, c) a processor that transforms the digital voltage data into digital surface charge density data, and d) a memory that stores the at least one electric potential $V_e$ and the transformed digital surface charge density data.

In some embodiments, the measuring and recording unit comprises electrodes configured to measure an electric potential $V_e$ when brought into contact with at least one part of the heart chamber.

In some embodiments, the measuring and recording unit comprises electrodes configured to measure an electric potential $V_e$ when not in contact with at least one part of the heart chamber.

The system can also comprise an imaging unit that represents the surface charge densities $\rho(P', t)$ as a 2-dimensional image or time-dependent sequence of images.

The system can comprise an imaging unit that represents the surface charge densities $\rho(P', t)$ as a 3-dimensional image or time-dependent sequence of images.

In accordance with another aspect of the invention, provided is a system that generates a table of dipole densities $v(P', t)$ of a given heart chamber, comprising:

a) a measuring and recording unit that measures and records data used to determine at least one electric potential $V_e$ at a given position P, b) an a/d-converter that converts the at least one electric potentials $V_e$ into digital voltage data, c) a processor that transforms the digital voltage data into dipole charge density data, and d) a memory that stores the at least one electric potential $V_e$ and the transformed dipole charge density data.

The measuring and recording unit can comprise electrodes configured to measure an electric potential $V_e$ when brought into con-tact with at least one part of the heart chamber.

The measuring and recording unit can comprise electrodes configured to measure an electric potential $V_e$ when not in contact with at least one part of the heart chamber.

The system can further comprise an imaging unit that represents the dipole densities $v(P', t)$ as a 2-dimensional image or time-dependent sequence of images.

The system can further comprise an imaging unit that represents the dipole densities $v(P', t)$ as a 3-dimensional image or time-dependent sequence of images.

The system can be configured to implement the above cited methods of the invention.

In a further aspect, the present invention is directed to a computer program comprising instructions for implementing a method of the present invention.

In a further aspect, the computer program of the invention can comprise instructions implementing a system of the invention.

The computer program of the present invention can comprise a computer readable program code executable by a processor, where the method can include starting program after booting a computer and/or a system in accordance with the invention.

A further aspect of the invention relates to a device for implementing a method according to the invention, comprising at least one an electrode for measuring the electrode potential $V_e$ using the method of contact mapping and/or using the method of non-contact mapping, at least one processing unit for generating and transforming $V_e$ into said surface charge density $\rho(P',t)$ and/or dipole density $\nu(P',t)$ for presenting on a display.

DRAWINGS

DETAILED DESCRIPTION OF ILLUSTRATIVE EMBODIMENTS

Research has indicated that the use of the surface charge densities (i.e. their distribution) or dipole densities (i.e. their distribution) to generate distribution map(s) will lead to a more detailed and precise information on electric ionic activity of local cardiac cells than potentials. Surface charge density or dipole densities represent a precise and sharp information of the electric activity with a good spatial resolution, whereas potentials resulting from integration of charge densities provide only a diffuse picture of electric activity. The electric nature of cardiac cell membranes comprising ionic charges of proteins and soluble ions can be precisely described by surface charge and dipole densities. The surface charge densities or dipole densities cannot be directly measured in the heart, but instead must be mathematically and accurately calculated starting from measured potentials. In other words, the information of voltage maps obtained by current mapping systems can be greatly refined when calculating surface charge densities or dipole densities from these.

The surface charge density means surface charge (Coulombs) per unit area (cm$^2$). A dipole as such is a neutral element, wherein a part comprises a positive charge and the other part comprises the same but negative charge. A dipole might represent the electric nature of cellular membranes better, because in biological environment ion charges are not macroscopically separated.

Figure 1:
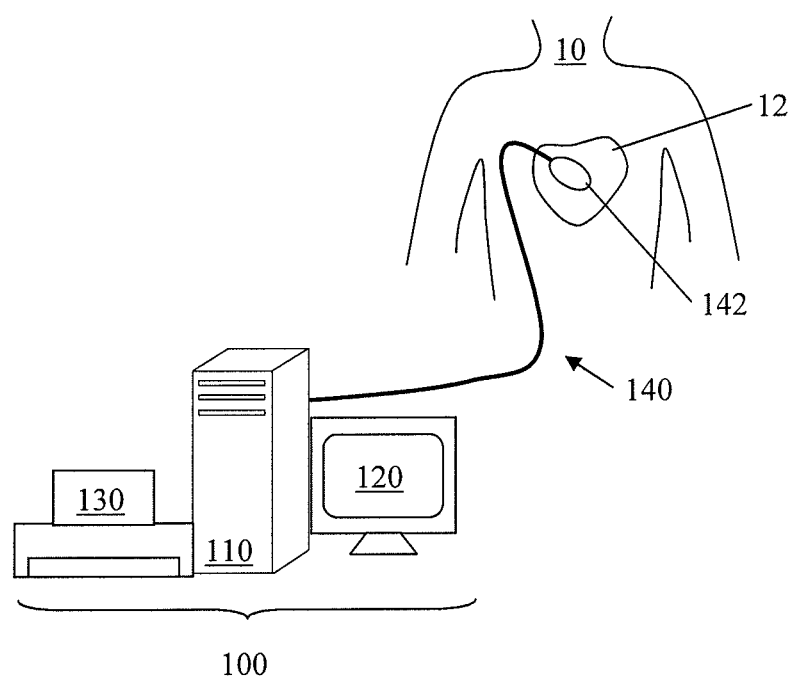
FIG. 1 is an exemplary embodiment of a mapping system, according to aspect of the present invention.

In order to generate a map of surface charge densities (surface charge density distribution) according to the present invention, the geometry of the given heart chamber must be known. The 3D geometry of the cardiac chamber is typically assessed by currently available and common mapping systems (so-called locator systems) or, alternatively, by integrating anatomical data from CT/MRI scans. FIG. 1 shows an example embodiment of a mapping system 100 that can be used to map a heart 12 of a human 10. Mapping system 100 can include a computer 110 having known types of input devices and output devices, such as a display 120 and printer 130, and a probe system 140. For the measurement of potentials the non-contact mapping method a probe electrode 142 will be used, which is connected to the computer 110 via a cable and forms part of probe system 140. The probe electrode 142 may be a multi-electrode array with elliptic or spherical shape. The spherical shape has certain advantages for the subsequent data analysis. But also other types or even several independent electrodes could be used to measure $V_e$. For example, when considering, for example, the ventricular cavity within the endocardium and taking a probe electrode with a surface $S_P$, which is located in the blood, it is possible to measure the potential $V(x,y,z)$ at point x,y,z on the surface $S_P$. In order to calculate the potential at the endocardial surface $S_e$ the Laplace equation:

$$\Delta V = \left(\frac{\partial^2}{\partial x^2} + \frac{\partial^2}{\partial y^2} + \frac{\partial^2}{\partial z^2}\right)V = 0 \qquad (1)$$

needs to be solved, wherein V is the potential and x,y,z denote the three dimensional coordinates. The boundary conditions for this equation are $V(x,y,z)=V_P(x,y,z)$ on $S_P$, wherein $V_P$ is the potential on surface of the probe.

The solution is an integral that allows for calculating the potential $V(x'y'z')$ at any point x'y'z' in the whole volume of the heart chamber that is filled with blood. For calculating said integral numerically a discretisation of the cardiac surface is necessary and the so called boundary element method (BEM) has to be used.

The boundary element method is a numerical computational method for solving linear integral equations (i.e. in surface integral form). The method is applied in many areas of engineering and science including fluid mechanics, acoustics, electromagnetics, and fracture mechanics.

The boundary element method is often more efficient than other methods, including the finite element method. Boundary element formulations typically give rise to fully populated matrices after discretisation. This means, that the storage requirements and computational time will tend to grow according to the square of the problem size. By contrast, finite element matrices are typically banded (elements are only locally connected) and the storage requirements for the system matrices typically grow quite linearly with the problem size.

With the above in mind, all potentials $V_P(x1',y1',z1')$ on the surface of the probe can be measured. To calculate the potential $V_e$ on the wall of the heart chamber, the known geometry of the surface of the heart chamber must be divided in discrete parts to use the boundary element method. The endocardial potentials $V_e$ are then given by a linear matrix transformation T from the probe potentials $V_P$: $V_e = T V_P$.

After measuring and calculating one or more electric potential(s) $V_e$ of cardiac cells in one or more position(s) $P(x,y,z)$ of the at least one given heart chamber at a given time t. The surface charge density and the dipole density is related to potential according to the following two Poisson equations:

$$\Delta V_e = \rho(P)\delta_{S_e}(P) \qquad (2)$$

$$\Delta V_e = \frac{\delta}{\partial n}(\nu \delta_{S_e}(P)) \qquad (3)$$

wherein $\rho(P)$ is the surface charge density in position P=x,y,z, $\delta_{S_e}(P)$ is the delta-distribution concentrated on the surface of the heart chamber $S_e$ and $\nu$ is the dipole density.

There is a well known relationship between the potential $V_e$ on the surface of the wall of the heart chamber and the surface charge (4) or dipole densities (5).

$$V_e(P) = -\frac{1}{4\pi}\int_{S_e} \frac{\rho(P')}{|P'-P|} d\sigma(P') \quad (4)$$

$$V_e(P) = \frac{1}{4\pi}\int_{S_e} \upsilon(P')\frac{\partial}{\partial n_{P'}} \frac{1}{|P-P'|} d\sigma(P') \quad (5)$$

(For a review see Jackson J D. Classical Electrodynamics, $2^{nd}$ edition, Wiley, N.Y. 1975.)

The boundary element method again provides a code for transforming the potential $V_e$ in formulas 4 and 5 into the desired surface charge densities and dipole densities, which can be recorded in the database.

In another embodiment of the method of the present invention the electric potential(s) $V_e$ is (are) determined by contact mapping. In this case the steps for calculating the electric potential $V_e$ are not necessary, because the direct contact of the electrode to the wall of the heart chamber already provides the electric potential $V_e$.

In a preferred embodiment of the method of the present invention the probe electrode comprises a shape that allows for calculating precisely the electric potential $V_e$ and, thus, simplifies the calculations for transforming $V_e$ into the desired charge or dipole densities. This preferred geometry of the electrode is essentially ellipsoidal or spherical.

In order to employ the method for determining a database table of surface charge densities of at least one given heart chamber in the context of the present invention, it is preferred to use a system comprising at least:

a) one unit for measuring and recording electric potentials V at a given position P(x,y,z) on the surface of a given heart chamber (Contact mapping) or a probe electrode positioned within the heart, but without direct wall contact (noncontact mapping)
b) one a/d-converter for converting the measured electric potentials into digital data,
c) one memory to save the measured and/or transformed data, and
d) one processor unit for transforming the digital data into digital surface charge density or dipole density data.

It is noted that numerous devices for localising and determining electric potentials of cardiac cells in a given heart chamber by invasive and non-invasive methods are well known in the art and have been employed by medical practitioners over many years. Hence, the method, system, and devices of the present invention do not require any particular new electrodes for implementing the best mode for practicing the present invention. Instead, the invention provides a new and advantageous processing of the available data that will allow for an increase in precision, accuracy and spatial resolution of cardiac activation mapping when compared to prior art systems based on electric surface potentials in the heart only. In the near future, the present invention will allow for providing superior diagnostic means for diagnosing cardiac arrhythmias and electric status of heart cells including metabolic and functional information.

Figure 2:
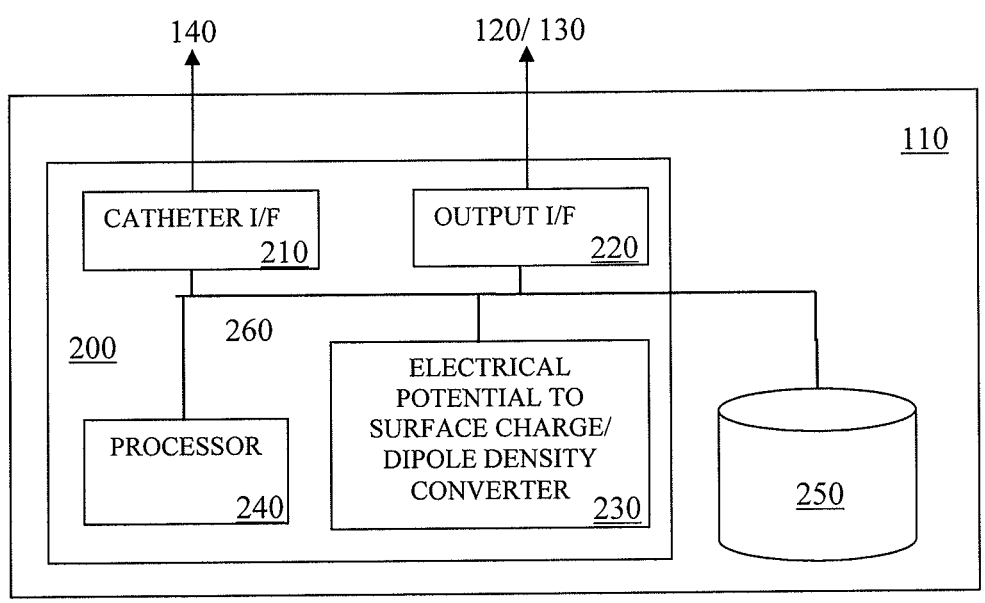
FIG. 2 is an exemplary embodiment of a computer architecture forming part of the mapping system of FIG. 1.

FIG. 2 provides an example embodiment of a computer architecture 200 that can form part of mapping system 100. Architecture 200 includes standard interface modules 210 for probe system 140 (and electrode 142) and standard interface modules 220 for interfacing with output devices 120, 130. The computer includes at least one processor 240 and at least one computer memory 250. The foregoing are generally known, however the present invention further includes an electrical potential to surface charge density and/or dipole density converter module 230. Module 230 includes instructions necessary for caring out the methods described herein, when executed by processor 240, wherein the results of such processing are stored in memory 250—as would be understood by one skilled in the art having the benefit of this disclosure.

Figure 3:
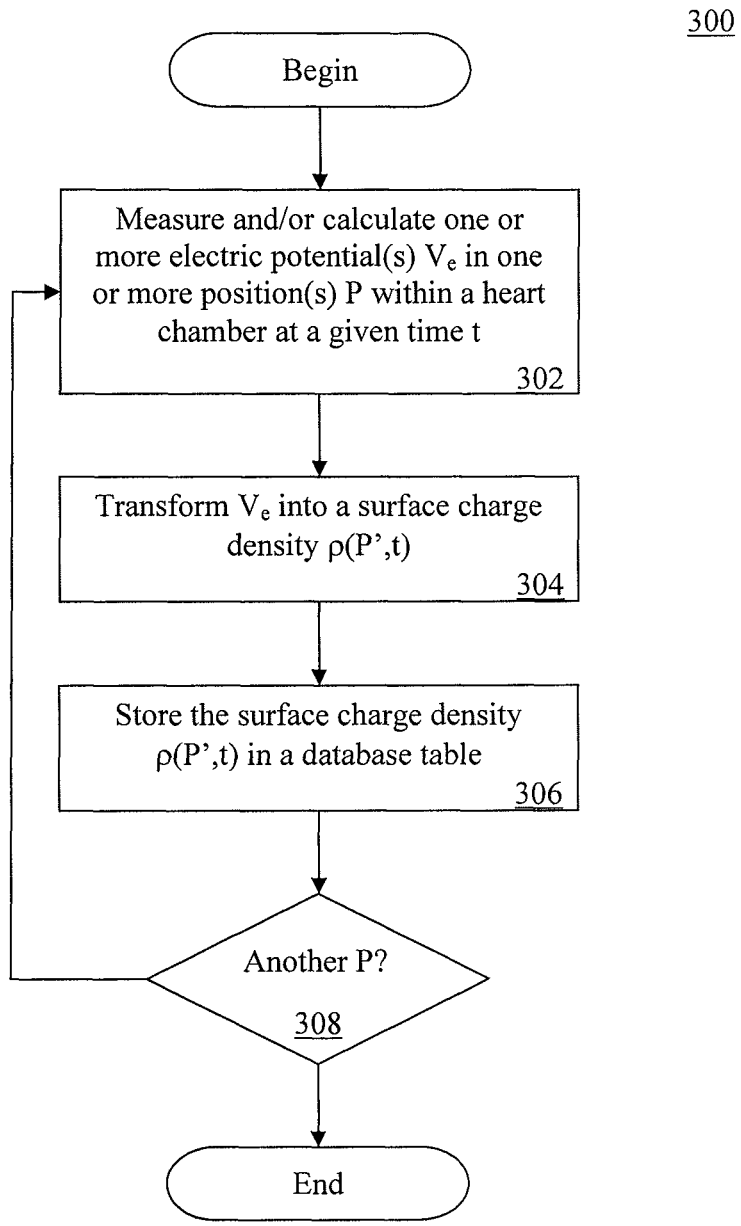
FIG. 3 is an example embodiment of a method of determining and storing surface charge densities, in accordance with aspects of the present invention.
Figure 4:
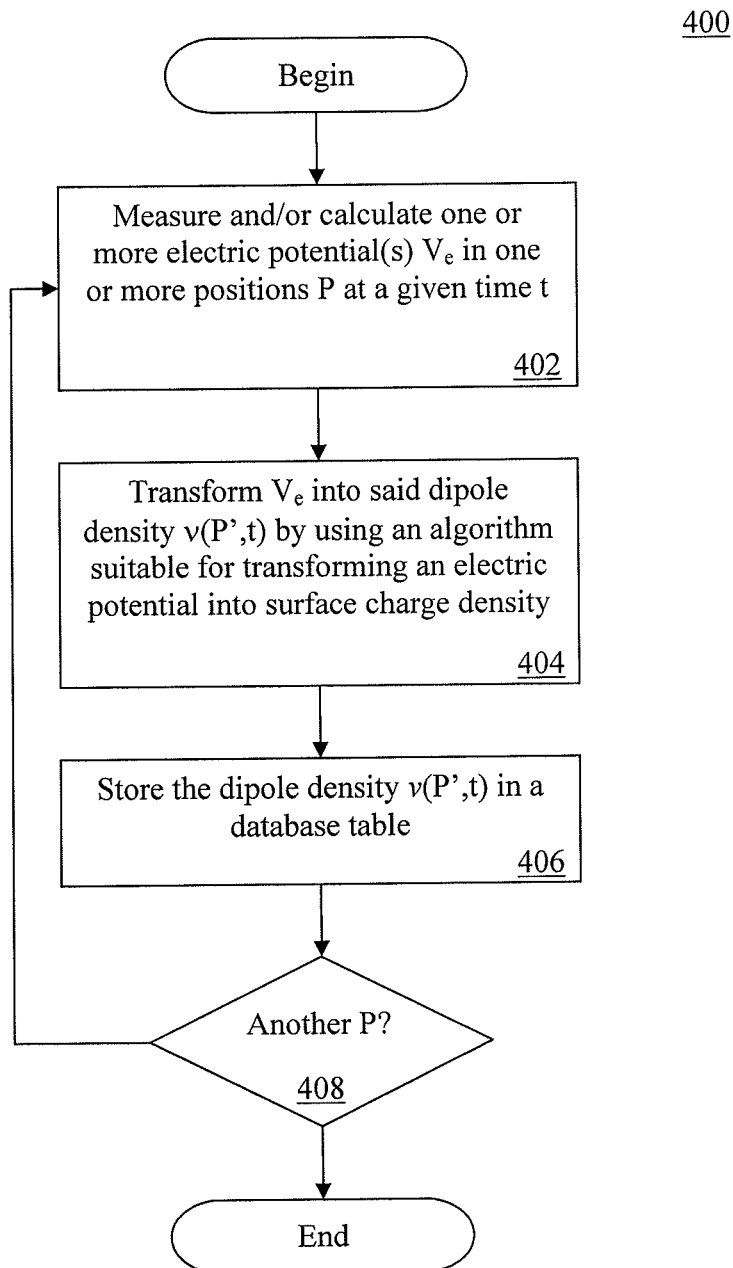
FIG. 4 is an example embodiment of a method of determining and storing dipole densities, in accordance with aspects of the present invention.

FIG. 3 and FIG. 4 summarize methods for determining and storing surface charge densities and dipole densities in accordance with aspects of the present invention, respectively, which have been described in detail above.

In method 300 of FIG. 3, in step 302, mapping system 100 is used to measure and/or calculate one or more electric potential(s) $V_e$ into one or more position(s) P within a heart chamber at a given time t. In step 304, $V_e$ is transformed into a surface charge density $\rho(P',t)$. In step 306, the surface charge density $\rho(P',t)$ is stored in a database table. The method is repeated if there is another P, in step 308.

In method 400 of FIG. 4, in step 402, mapping system 100 is used to measure and/or calculate one or more electric potential(s) $V_e$ in one or more position(s) P within a heart chamber at a given time t. In step 404, $V_e$ is transformed into said dipole density $\upsilon(P',t)$ by using an algorithm suitable for transforming an electric potential into surface charge density. In step 406, the dipole density $\upsilon(P',t)$ is stored in a database table. The method is repeated if there is another P, in step 408.

While the foregoing has described what are considered to be the best mode and/or other preferred embodiments, it is understood that various modifications may be made therein and that the invention or inventions may be implemented in various forms and embodiments, and that they may be applied in numerous applications, only some of which have been described herein. It is intended by the following claims to claim that which is literally described and all equivalents thereto, including all modifications and variations that fall within the scope of each claim.

What is claimed is:

1. A method for generating a database table of surface charge densities $\rho(P',t)$ that embody an ionic nature of cellular membranes across a cardiac wall of at least one given heart chamber, the cellular membrane surface charge density information comprising a table $\rho(P',t)$ wherein:

i) a position P'=(x',y',z') of a point on the cellular membrane of the cardiac wall of a heart chamber is defined in x, y, z-coordinates,
ii) t is a time of measurement for said cellular membrane surface charge density, and
iii) $\rho$ is the cellular membrane surface charge density at said time t and said position P' derived from a measured electric potential, the method comprising the following steps:
a) determining electric potential data $V_e$ at locations P at a given time t using a plurality of electrodes,
b) transforming the electric potential data $V_e$ into said cellular membrane surface charge density $\rho(P',t)$ at positions P' on the cardiac wall using a processor executing a set of conversion instructions stored in a computer memory, and
c) storing each cellular membrane surface charge density in the computer memory as a table of cellular membrane surface charge densities,
wherein transforming the electric potential data $V_e$ into the cellular membrane surface charge density ($\rho$) in step b) employs a boundary element method (BEM).

2. The method according to claim 1, where the electrical potential data $V_e$ is determined by contact mapping.

3. The method according to claim 1, where the electrical potential data $V_e$ is determined by non-contact mapping.

4. The method according to claim 1, where a geometry of the plurality of electrodes used in determining the electrical potential data $V_e$ is ellipsoidal.

5. The method according to claim 1, where a geometry of the plurality of electrodes used in determining the electrical potential data $V_e$ is spherical.

6. The method according to claim 1, wherein said electric potential data $V_e$ is transformed into the cellular membrane surface charge densities ρ using the following equation:

$$V_e(P) = -\frac{1}{4\pi} \int_{S_e} \frac{\rho(P')}{|P'-P|} d\sigma(P')$$

Wherein:
S$_e$=surface of the cardiac wall;
P'=integration variable running over the entire cardiac wall; and
P=position of the measuring electrode.

7. A method for generating a database table of dipole densities ν(P',t) that embody an ionic nature of cellular membranes across a cardiac wall of at least one given heart chamber, the cellular membrane dipole density information comprising a table ν(P', t) wherein:
 i) a position P'=(x',y',z') of a point on the cellular membrane of the cardiac wall of a heart chamber is defined in x, y, z-coordinates,
 ii) t is a time of measurement for said cellular membrane dipole density, and
 iii) ν is the cellular membrane dipole density at said time t and said position P' derived from a measured electric potential,
the method comprising the following steps:
 a) determining electric potential data $V_e$ at locations P at a given time t using a plurality of electrodes;
 b) transforming the electric potential data $V_e$ into said cellular membrane dipole density ν(P',t) at positions P' on the cardiac wall using a processor executing a set of conversion instructions stored in a computer memory; and
 c) storing each cellular membrane dipole density in the computer memory as a table of cellular membrane dipole densities,
wherein transforming the electric potential data $V_e$ into the cellular membrane dipole density (ν) in step b) employs a boundary element method (BEM).

8. The method according to claim 7, wherein the electrical potential data $V_e$ is determined by contact mapping.

9. The method according to claim 7, wherein the electrical potential data $V_e$ is determined by non-contact mapping.

10. The method according to claim 7, wherein a geometry of the plurality of electrodes used in determining the electrical potential data $V_e$ is ellipsoidal.

11. The method according to claim 7, wherein a geometry of the plurality of electrodes used in determining the electrical potential data $V_e$ is spherical.

12. The method according to claim 7, wherein said electric potential data $V_e$ is transformed into the cellular membrane dipole densities ν using the following equation:

$$V_e(P) = \frac{1}{4\pi} \int_{S_e} \nu(P') \frac{\partial}{\partial n_{P'}} \frac{1}{|P-P'|} d\sigma(P')$$

Wherein:
S$_e$=surface of the cardiac wall,
P'=integration variable running over the entire cardiac wall, and
P=position of the measuring electrode.

13. A system that generates a table of surface charge densities ρ(P',t) that embody an ionic nature of cellular membranes across a cardiac wall of a given heart chamber, comprising:
 a) a measuring and recording unit that measures and records electrical potential data $V_e$ at given positions P;
 b) an a/d-converter that converts the electrical potential data $V_e$ into digital voltage data;
 c) processor that transforms the digital voltage data into digital cellular membrane surface charge density data; and
 d) a memory that stores the electrical potential data $V_e$ and the transformed digital cellular membrane surface charge density data.

14. The system of claim 13, wherein the measuring and recording unit comprises electrodes configured to measure the electrical potential data $V_e$ when brought into contact with at least one part of the heart chamber.

15. The system of claim 13, wherein the measuring and recording unit comprises electrodes configured to measure the electric potential data $V_e$ when not in contact with at least one part of the heart chamber.

16. The system of claim 13, further comprising:
an imaging unit that represents the cellular membrane surface charge densities ρ(P',t) as a 2-dimensional image or time-dependent sequence of images.

17. The system of claim 13, further comprising:
an imaging unit that represents the cellular membrane surface charge densities ρ(P',t) as a 3-dimensional image or time-dependent sequence of images.

18. A system that generates a table of dipole densities ν(P',t) that embody an ionic nature of cellular membranes across a cardiac wall of a given heart chamber, comprising:
 a) a measuring and recording unit that measures and records electrical potential data $V_e$ at given positions P;
 b) an a/d-converter that converts the electrical potential data $V_e$ into digital voltage data;
 c) processor that transforms the digital voltage data into digital cellular membrane dipole density data; and
 d) a memory that stores the electrical potential data $V_e$ and the transformed digital cellular membrane dipole density data.

19. The system of claim 18, wherein the measuring and recording unit comprises electrodes configured to measure the electrical potential data $V_e$ when brought into contact with at least one part of the heart chamber.

20. The system of claim 18, wherein the measuring and recording unit comprises electrodes configured to measure the electric potential data $V_e$ when not in contact with at least one part of the heart chamber.

21. The system of claim 18, further comprising:
an imaging unit that represents the cellular membrane dipole densities ν(P',t) as a 2-dimensional image or time-dependent sequence of images.

22. The system of claim 13, further comprising:
an imaging unit that represents the cellular membrane dipole densities $\nu(P',t)$ as a 3-dimensional image or time-dependent sequence of images.

* * * * *